United States Patent
Da Silva et al.

(10) Patent No.: US 6,729,336 B2
(45) Date of Patent: May 4, 2004

(54) IN-STENT RESTENOSIS DETECTION DEVICE

(75) Inventors: Luiz B. Da Silva, Danville, CA (US); Victor C. Esch, San Francisco, CA (US); Alexander M. Rubenchik, Livermore, CA (US); Jonathan Hares, Wallingford (GB); Joseph D. Kilkenny, Livermore, CA (US); Gilbert W. Collins, Livermore, CA (US); Paul J. Weber, Fort Lauderdale, FL (US)

(73) Assignee: Pearl Technology Holdings, LLC, Livermore, CA (US)

( * ) Notice: Subject to any disclaimer, the term of this patent is extended or adjusted under 35 U.S.C. 154(b) by 190 days.

(21) Appl. No.: 10/109,150

(22) Filed: Mar. 28, 2002

(65) Prior Publication Data

US 2003/0100815 A1 May 29, 2003

Related U.S. Application Data

(63) Continuation-in-part of application No. 09/995,284, filed on Nov. 27, 2001.

(51) Int. Cl.$^7$ .............................................. A61B 19/00
(52) U.S. Cl. ..................................... 128/897; 128/899
(58) Field of Search ........................... 600/9, 454, 459, 600/500, 504, 505; 128/897–99; 607/60, 61, 62, 65

(56) References Cited

U.S. PATENT DOCUMENTS 6,233,479 B1 * 5/2001 Haddad et al. ............. 600/430
6,308,715 B1 * 10/2001 Weissman et al. .......... 128/899

* cited by examiner

Primary Examiner—John P. Lacyk
(74) Attorney, Agent, or Firm—John P. Wooldridge

(57) ABSTRACT

A medical device is described that can be used to detect in stent restenosis. This invention consists of a stent of current or modified technology, an electromagnetic wave transmitter to excite the stent and an acoustic sensor to detect stent acoustic oscillations.

26 Claims, 4 Drawing Sheets

IN-STENT RESTENOSIS DETECTION DEVICE

The application is a continuation-in-part of U.S. patent application Ser. No. 09/995,284, titled "In-Stent Restenosis Detection Device", filed Nov. 27, 2001, pending incorporated herein by reference.

BACKGROUND OF THE INVENTION

1. Field of the Invention

The present invention relates to a medical device that can be used to evaluate in-stent restenosis. The present invention also relates to a combination electromagnetic wave excitation and ultrasound detection device that can be used to monitor occlusions inside implanted stents.

2. Description of Related Art

An estimated seven million Americans suffer from coronary artery disease, which causes 1.5 million myocardial infarctions (heart attacks) and over half a million deaths annually at a cost of over $100 billion. Coronary artery disease results from atherosclerosis, a complex process in which fatty and other deposits (e.g., cellular intimal and mineral additives, and engrained proteinaceous or clotting/platelet debris) build up in the walls of arteries, resulting in blockages and reduced blood flow. This process leads to the formation of a plaque of atherosclerotic material that can be comprised of various cells, lipids (fats or cholesterol), and collagen (fibrous tissue). This process progresses over a number of years and may eventually result in the formation of a blockage (stenosis) in the coronary artery. If the artery is sufficiently narrowed, blood flow is reduced (ischemia), and chest pain (angina pectoris), heart attack, or sudden death may follow. In addition to the narrowing produced by atherosclerosis, plaques may also rupture, resulting in the formation of a thrombus (clot) on the plaque surface, leading to an abrupt cessation of blood flow to the heart. Plaque rupture plays a key role in most cases of heart attack and stroke.

In 1977, Dr. Andreas Gruentzig from Switzerland introduced a novel method for treating coronary artery stenosis, which he termed "Percutaneous Transluminal Coronary Angioplasty" (PTCA), also commonly known as balloon angioplasty. Over 500,000 coronary angioplasties (the term angioplasty is derived from angio, which refers to a blood vessel, and plasty, which means to reshape) were performed in the U.S., surpassing the number of coronary bypass operations. The advantage of this technique is that it can be performed using minimally invasive catheter procedures. Using special x-ray equipment and contrast dye to visualize the arteries, the cardiologist advances a guide catheter (hollow tube) through a vascular access sheath and up the aorta to the origin of the coronary arteries. Using this catheter as a track to the coronary artery, a long, fine guidewire (generally 0.014 inches in diameter) is negotiated across the stenosis. A catheter with a deflated balloon on the far end is then advanced over the guidewire to the narrowed arterial segment. At this point the balloon is inflated and the occluding plaque compressed to the arterial wall.

In conventional PTCA the occluding plaque is simply compressed and no material is removed. In about one-third of cases, re-narrowing of the treated segment may occur over a period of several months, necessitating a repeat procedure or coronary artery bypass surgery. This re-narrowing is termed "restenosis" and appears to be distinct from the process of atherosclerosis. Despite intense research efforts and numerous drug trials, a solution to this problem remains elusive.

In order to reduce the restenosis rate and improve blood flow, stents are now routinely inserted into arteries after PTCA. Stents are wire mesh tubes usually made of metal that are expanded within the artery to form a scaffold that keeps the artery open. The stent stays in the artery permanently, holds it open, improves blood flow to the heart muscle and relieves symptoms (usually chest pain).

After placement, the stent will normally be covered with epithelium over the course of several weeks. In the case of in-stent restenosis, this tissue growth process continues. The hyperproliferation of normal cells results in the obstruction of the flow of blood through the stented vessel. Even with stents, the restenosis rate can be as high as 25%.

Restenosis within the stent can be detected in several ways. If a patient is symptomatic with angina, several diagnostic procedures may be performed. Stress Echo Cardiography may be performed whereby the heart is imaged using ultrasound, and differences between the motion of the resting heart and the exercised heart are used to determine abnormalities that indicate restricted blood flow. Unfortunately this test typically cannot detect a blockage less than 50%. A Thallium Stress Test may also be performed to indicate the degree of blood supply to the heart under differing load conditions (at rest or exercised). Unfortunately, this procedure requires injecting radioactive markers into the patient and the use of expensive gamma imaging cameras and requires above 70% blockage of blood flow to give a positive result Stress Echo Cardiography and Thallium Stress Tests are expensive, and can subject a patient with a dysfunctional heart to exercise loads, which can be dangerous.

If preliminary test results are positive then a physician generally performs coronary angiography. In this procedure a catheter is inserted into the patient and x-ray contrast agent injected so that the blood flow can be imaged with x-rays. This is an invasive procedure requiring the use of an operating room and exposes the patient to x-ray radiation. The procedure is also very costly. In addition there is a finite risk that the patient will experience a stroke or other adverse event that is associated with the procedure, and this risk can extend long period after the angiography is performed.

Another emerging technique, referred to as "intravascular ultrasound" where a miniature ultrasound transducer is inserted by a catheter and the acoustic impedance of the blood vessel is monitored by external acoustic receivers is also being evaluated for efficacy. Unfortunately this is an invasive procedure.

Recently Spillman et al. (WO 00/56210) and Cimochowski et al. (WO 99/26530) described a novel stent design that incorporates a miniature sensor that can be used to measure flow or pressure and diagnose restenosis. Unfortunately, these devices require incorporating a sensor into the stent that could adversely affect the mechanical properties of the stent.

Given the limitations of current techniques to diagnose restenosis, there is a need for a novel device that can safely, quickly and effectively detect restenosis after stenting. The present invention fulfills this need, and further provides related advantages.

SUMMARY OF THE INVENTION

An object of the present invention is to provide a device and method to evaluate in-stent restenosis.

Another object of the present invention is to provide an endoluminal implant (or stent) that can be inserted into the body and excited by electromagnetic radiation to oscillate.

Another object is to provide an ultrasound transducer that detects the excited ultrasound oscillations for analysis to detect a change in the aperture (i.e., lumen) for blood flow within the stent.

These and other objects will be apparent to those skilled in the art based on the disclosure herein.

There are several possible approaches to detecting in-stent restenosis according to the present invention. Stent structures have characteristic resonant behavior in their interaction with electromagnetic and or acoustic energy. These resonance features are influenced by the dimensions, structure, materials of the stent, as well as other features of the stent itself, and the surrounding materials and structures. Thus electromagnetic and or acoustic energy may be utilized to determine the physical properties of the stent itself, and the materials surrounding and enclosed by the stent.

The approaches to determining the in-stent restenosis may include, but are not limited to, the following:

1. RF excitation, Probing RF resonant modes, Detecting RF radiation. Using Radio Frequency EM energy to interrogate the stent, the frequency of the RF energy is scanned, and the response of the stent is detected, in reflection, absorption, scatter, or other characteristic EM phenomena, by detecting the modified RF energy. This includes the detection of shifted frequencies that are produced by modifications to the stent, e.g., a printed circuit upon the surface of the stent. This may also include modifications to the stent structure to enhance sensitivity to restenosis material, and or to enhance the interaction with the RF energy. These modifications can include mechanical modifications, such as shapes, wire mesh patterns, such as fractal patterns, mechanical features, within cylindrical form, or extending out of a cylindrical and into the lumen. To enhance the measurement, stent materials may be coated, surface treated, or otherwise modified for insulative behavior. Additionally, active electronic devices may be incorporated, either integrated upon or in the stent, or added discretely to the stent.

2. RF excitation, within an RF resonant absorption, RF modulation at frequencies consistant with stent acoustic modes to search for resonant acoustic modes, Detection of acoustic energy. The stent acoustic modes may be excited through various phenomena, including Lorentz forces or ohmic heating. The stent may be modified, as previously mentioned, to enhance RF interaction, as well as and including modifications that enhance the sensitivity of the acoustic modes to restenosis, and or to the generation of acoustic energy.

3. Exciting the stent with RF energy that is modulated within an acoustic resonance of the structure, in order to enhance acoustic output of the stent, and scanning the RF carrier frequency to seek the characteristic RF modes of the stent, detecting the modes through the acoustic energy emission. As previously stated, the stent may be modified to enhance the acoustic and or EM interaction, and the sensitivity to restenosis.

4. Exciting the stent with RF energy, and directly detecting the acoustic energy of the stent modes. This is simply the limiting case of exciting acoustic modes whose frequency corresponds to the RF frequency. All the previously mentioned stent modifications may be employed. In this case the enhancements may be required to optimize the coincidence of optimal RF interaction with a frequency of optimal acoustic interaction, or vice versa.

For treating coronary occlusions, the endoluminal implant is generally a tubular shaped member having at least two configurations. Initially it has a compact configuration in which the member has a cross-sectional size smaller than the lumen at the treatment area. After placement it has an expanded configuration in which the member has a cross-sectional size comparable to the lumen of the treatment area. The implant includes at least a portion that is made of an electrical conducting material.

The endoluminal implant system further includes an external electromagnetic wave generator/transmitter and an ultrasound detector. A modulated EM wave generates a force as a result of the cross product of the induced azimuthal current and the longitudinal magnetic field. This J×B force induces a radial oscillation within the stent. The radial oscillations are a maximum when the frequency (or modulation frequency) of the EM wave is in resonance with the characteristic acoustic frequencies of the stent. In one embodiment the patient's chest is placed between a pair of coils or near an antenna and the stent excited over a range of EM wave frequencies and modulation frequencies. The EM wave range of frequencies is selected to effectively couple energy into the stent (e.g., 100 MHz–10 GHz). The modulation frequencies range is selected to cover the characteristic acoustic resonance frequencies of the stent (e.g., 100 kHz-1 MHz). The ultrasound (or acoustic) detector measures the generated acoustic signal as a function of the EM wave frequencies. The measured acoustic spectrum will change when in-stent restenosis occurs.

During EM wave excitation the stent is also heated through resistive heating. The resulting heating causes thermal expansion of the stent, which also excites acoustic oscillations. The modulation frequency of the EM waves will control what acoustic frequencies are excited. In order to avoid an uncontrolled rise in temperature, the cooling time of the stent needs to be less than or comparable to the low modulation frequency of the EM wave. The cooling of the stent is controlled by thermal conduction and can be estimated by $\tau \approx x^2/4D$, where x is the stent wire thickness and D is the thermal diffusivity. For steel and x=50 microns, $\tau \sim 50$ microseconds. Under these conditions the primary acoustic harmonic would be approximately 200 kHz. In order to increase the possible frequency the stent could have a thin high thermal conductivity coating (e.g. diamond) that would reduce the cooling time.

In another embodiment the natural blood flow through the stent is used to excite the resonant acoustic modes of the stent. The measured blood pressure (and thus the measured force on the stent caused by forced blood flow) contains noise at frequencies much higher than the pulse frequency due to the complicated blood flow through the stent. This noise spectrum will have a small component overlapping with the natural resonant acoustic mode of the stent. In addition to the pressure of the natural blood flow, there is a net magnetic flux through the stent. This magnetic flux will also induce a current into a conducting stent, again causing a J×B force proportional to the amount of blood flow. This too will create a small acoustic excitation of the stent, which may be detected. In these cases the resonant acoustic signal would be detected without RF excitation.

The restenosis of a stent may be detected through the interrogation of the acoustic or electromagnetic properties of the stent, or an interrogation of a combination of the acoustic and EM properties. Because of the changes in the materials resident in, or flowing through the stent, the fundamental acoustic and EM modes of the stent change as the material loading changes.

The acoustic oscillations of the stent, excited directly by RF EM radiation, or modulation of an RF carrier, satisfy the wave equation $$\Delta_r \phi + \chi^2 \phi = 0; \quad \chi^2 = \frac{\omega^2}{s^2} - k_z^2; \quad \phi \propto e^{-i\omega t + ik_z z} \tag{1}$$

where $\omega$ is the sound frequency, s is the sound speed, and $k_z$ is the wavenumber. The natural boundary condition is $$\frac{\partial \phi}{\partial r} = 0 \text{ at } r = a.$$

Here a is the stent radius and s is the sound speed. The localized solution of (6) is given by $$\phi = A J_n(\chi r) e^{in\phi} \tag{2}$$

where $J_n$ is the Bessel function of order n. The minimal value of $\chi = 1.84/a$ is reached for n=0 and for $k_z=0$. The corresponding minimal sound frequency is $$\omega_0 = \frac{1.84 s}{a} \tag{3}$$

For s=1550 m/sec (sound speed in blood) and the stent radius a=1 mm, the sound frequency v $$v = \frac{\omega_0}{2\pi} \approx 454 \text{ kHz}.$$

This frequency and its harmonics are weakly attenuated in tissue and will therefore propagate through the surrounding tissue. The finite length of the cylinder increases the frequency by a value $\delta\omega$ $$\frac{\delta\omega}{\omega} \sim \frac{a^2}{L^2} \tag{9}$$

The growth of tissue on the stent wall will produce a frequency shift $\delta\omega_f$ equal to $$\frac{\delta\omega_f}{\omega} = \frac{\int \delta s^2 \phi^2 dV}{s^2 \int \phi^2 dV} \sim \frac{\delta s^2}{s^2} \frac{h}{a} \tag{4}$$

where h is the tissue thickness and $\delta s^2$ is the difference of the squares of the sound speeds in plaque and blood. The difference in sound speed between blood and fat can be as high as 200 m/sec (15%). The resulting frequency shift can be as high as 80 kHz (20%) for 50% occlusions. The spectrum of the ultrasound generated by the stent will have a cut off at frequency $\omega_0$ with no sound generation below $\omega_0$. Since stents currently in use have a variety of structures and geometries, the acoustic spectrum will generally exhibit multiple broad peaks.

Another technique that can enhance sensitivity when the acoustic frequency is different than the RF absorption frequency is to sweep the RF frequency past the EM resonant modes of the stent while detecting the acoustic response. Again the acoustic response is excited through modulation of the carrier. The exact value and shift of the RF eigen-frequency can be optimized by careful selection of the stent design. As an example of the sensitivity of the RF absorption frequency to restenosis, assume the stent is a cylinder of finite size resonating with its characteristic minimal H-mode. The minimal H-mode eigen-frequency for a metal cylinder of radius a is given by $$f = 1.84 \frac{c}{2\pi a \sqrt{\varepsilon}} \tag{1}$$

Blood has a high refractive index, $\sqrt{\varepsilon} \sim 8$, for f<10 Ghz. Therefore, a blood filled cylinder with a=0.1 cm gives f~11 GHz. As plaque or a thrombus forms on the stent, the dielectric constant inside the resonator changes by $\delta\varepsilon$ resulting in a shift in the eigen-frequency. The frequency shift is given by $$\frac{\delta f}{f} = \frac{\int |E|^2 \delta\varepsilon dV}{2\varepsilon \int |E|^2 dV} \sim \frac{\delta\varepsilon h}{\varepsilon a} \tag{2}$$

Here E is the electric field distribution for the lowest H mode and $\delta\varepsilon$ is the variation of dielectric constant within the stent. Given the difference between stenotic tissue and blood, frequency shifts of several percent are possible.

In one possible method to treat and monitor coronary occlusions, a physician inserts the endoluminal implant (stent) into the patient using a balloon catheter. After the procedure is completed or within a month, the patient is placed in proximity to the EM transmitter and the ultrasound transducer is positioned on the skin near the stent. The EM transmitter frequency is tuned to a frequency that is known, or has been measured, to deposit energy effectively in the stent under test. The RF source is then modulated over a frequency range (e.g., 100 kHz to 2 MHz), which encompasses the characteristic acoustic response that is affected by restenosis, and the ultrasound signal as a function of modulation frequency is measured. The ultrasound amplitude is sensitive to the stent geometry and therefore the signal will have a structure characteristic of the deployed stent. This data is collected and recorded to provide a baseline frequency response around the acoustic frequencies of natural resonance of the stent for the patient with no restenosis. In subsequent months the patient visits the doctor's office and a new frequency response is measured. The new frequency response is compared to the baseline frequency response and any previous measurements to identify possible restenosis. When the change in the frequency response exceeds some predetermined limit, the doctor can be advised to perform additional tests including angiography.

In another possible method to treat and monitor coronary occlusions, a physician inserts the endoluminal implant (stent) into the patient using a balloon catheter. After the procedure is completed or within a month, the patient is placed in proximity to the EM transmitter and the ultrasound transducer is positioned on the skin near the stent. The EM transmitter frequency is tuned to a frequency that is known, or has been measured, to deposit energy effectively in the stent under test. The RF source is then modulated at a frequency that is known to, or has been measured to, produce adequate acoustic signals. The RF frequency is then scanned, with fixed modulation, and the acoustic signal is recorded as a function of RF frequency. The RF scattered radiation is sensitive to the stent geometry and therefore the signal will have a structure characteristic of the deployed stent. This data is collected and recorded to provide a baseline frequency response around the RF frequencies of natural resonance of the stent for the patient with no restenosis. In subsequent months the patient visits the doctor's office and a new frequency response is measured. The new frequency response is compared to the baseline frequency response and any previous measurements to identify possible restenosis. When the change in the frequency response exceeds some predetermined limit, the doctor can be advised to perform additional tests including angiography.

Although this technique is applicable to existing metallic stents, alternative stent designs can enhance the RF/acoustic signal and exhibit a narrow resonance frequency that can be more sensitive to plaque formation. For example, the stent can have an imprinted resonance circuit tuned to a suitable RF frequency for easy coupling. In this case the resonant RF frequency of the stent will also change with restenosis formation due to the change in dielectric constant inside both the coil and near the fringe field of the patterned capacitors. Another approach to enhance the EM stent coupling is to manufacture the stent using a Fractal antenna design that can widen the frequency sensitivity of the stent. Another approach to enhance the EM stent coupling is to manufacture the stent with at least a core and an outer layer. The inner core of the stent material is a conductive metal (e.g., steel, titanium, Nitinol, gold, platinum) and the outer layer is an insulating dielectric (e.g., titanium oxide, silicon nitride, diamond, biocompatible polymers).

A combination of scanning RF frequency, and RF modulation, for the detection of acoustic modes and or EM modes of the stent, may provide additional and complimentary information for the determination of the characteristics of the stent, including degree of restenosis.

In order to improve the signal to noise, the simple ultrasound transducer can be replaced by an imaging ultrasound transducer that only collects ultrasound energy from the area near the stent. This technique can be used to reduce acoustic oscillations generated due to thermal heating of tissue in other areas of the body.

The use of low power electromagnetic waves makes this device safe for the patient and eliminates the need for unnecessary x-ray imaging. To increase the signal to noise, the device can be synchronized to the natural rhythmic variations of the patient such as heart beat rate. These slight modifications are easily adapted into the device.

The human body presents particular difficulties in the localization and distribution of RF electromagnetic energy. Because of the many surfaces and interfaces within the body, for example ribs, lungs, various other organs, fat and muscle layers, the distribution of RF energy tends to be very inhomogeneous. It may happen that very little intensity is incident upon the stent, while adjacent areas are well illuminated. To enhance the distribution of the radiation, a phased array antenna system may be used, such as a microstrip antenna, or patch type antenna, whereby the phases of the individual antenna components may be modified in order to target the electromagnetic energy onto the stent. This may be done in a time-averaged way, to uniformly illuminate all tissue in the vicinity of the targeted stent, or in a prescribed fashion in order to tailor the phases in a manner to optimize the intensity on the stent. The feedback of the detected acoustic signal, or detected scattered or reflected RF, may be used to guide the phase given to each of the individual elements of the array. Alternatively, a phase plate, which may be individually tailored, or pre-made, can be placed in front of a patient to place a phase front on the RF wavefront so as to enhance the RF upon the stent.

In a similar fashion, an index-matching interface may be placed upon the patient in order to effectively couple the RF into the patient, and out of the patient. The layer materials, especially chosen for their index of refraction at the RF frequencies, and thickness, e.g., quarter wave, as well as the number of layers, may be chosen to optimize the coupled RF. These and other objects will be apparent to those skilled in the art based on the teachings herein. Other objects and advantages of the present invention will become apparent from the following description and accompanying drawings.

BRIEF DESCRIPTION OF THE DRAWINGS

The accompanying drawings, which are incorporated into and form part of this disclosure, illustrate embodiments of the invention and together with the description, serve to explain the principles of the invention.

DETAILED DESCRIPTION OF THE INVENTION

Figure 1:
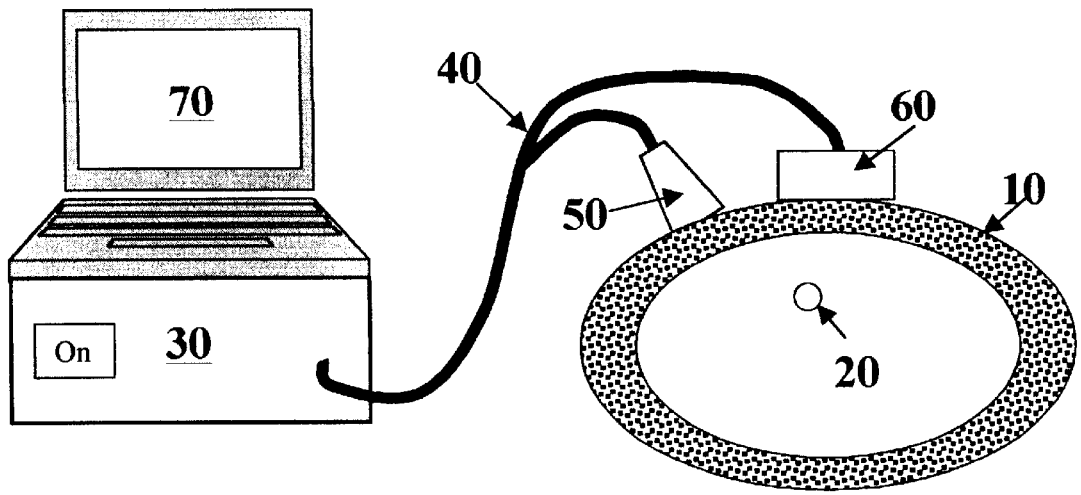
FIG. 1 illustrates an embodiment of the system and how it would be used in accordance with the present invention.

Embodiments of the present invention utilize an electromagnetic wave (EM) transmitter (100 MHz–1 GHz) to excite acoustic oscillations in a stent that are then detected using an ultrasound transducer. FIG. 1 shows the key components of an embodiment of the system. The system includes an electronic control unit 30 that is connected through a cable 40 to an electromagnetic wave transmitter 50 and an ultrasound detector 60. The electromagnetic wave is transmitted through the chest of the patient 10 and excites the implanted stent 20. When excited the implanted stent 20 generates acoustic waves that are detected by the ultrasound detector 60. The control unit 30 can generate electromagnetic waves over a wide frequency range that can be effectively coupled into the conductive stent 20. The control unit 30 can include a computer for data analysis, and archiving. A monitor 70 is used to guide the user and display results.

Figure 2:
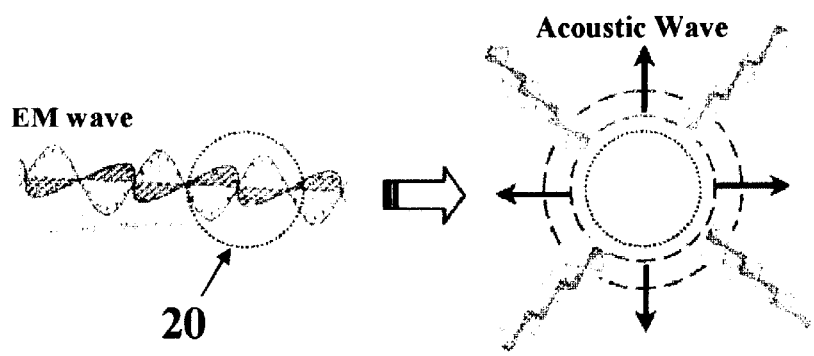
FIG. 2 illustrates the basic concepts of an embodiment of the present invention.

FIG. 2 illustrates the basic underlying concept of the present invention. A modulated EM wave is transmitted through the patient and interacts with a stent 20. The interaction of the EM wave with the stent generates a force as a result of the cross product of the induced azimuthal current and the longitudinal magnetic field. This J×B force induces a radial oscillation within the stent. The induced currents can also heat the metallic stent 20 and induce thermal expansion of the stent, which also generates acoustic oscillations. The radial oscillations are a maximum when the frequency (or modulation frequency) of the EM wave is in resonance with the characteristic acoustic frequencies of the stent. The acoustic spectrum is sensitive to stent configuration and the properties of surrounding tissue. The change in acoustic spectrum is used by the present invention to identify restenosis.

The EM waves can be transmitted into the patient's chest using a pair of coils on either side of the patient, a single coil, fractal antenna, open dipole transmitter, patch antenna, or other antennas, which are common to the art.

Figure 3:
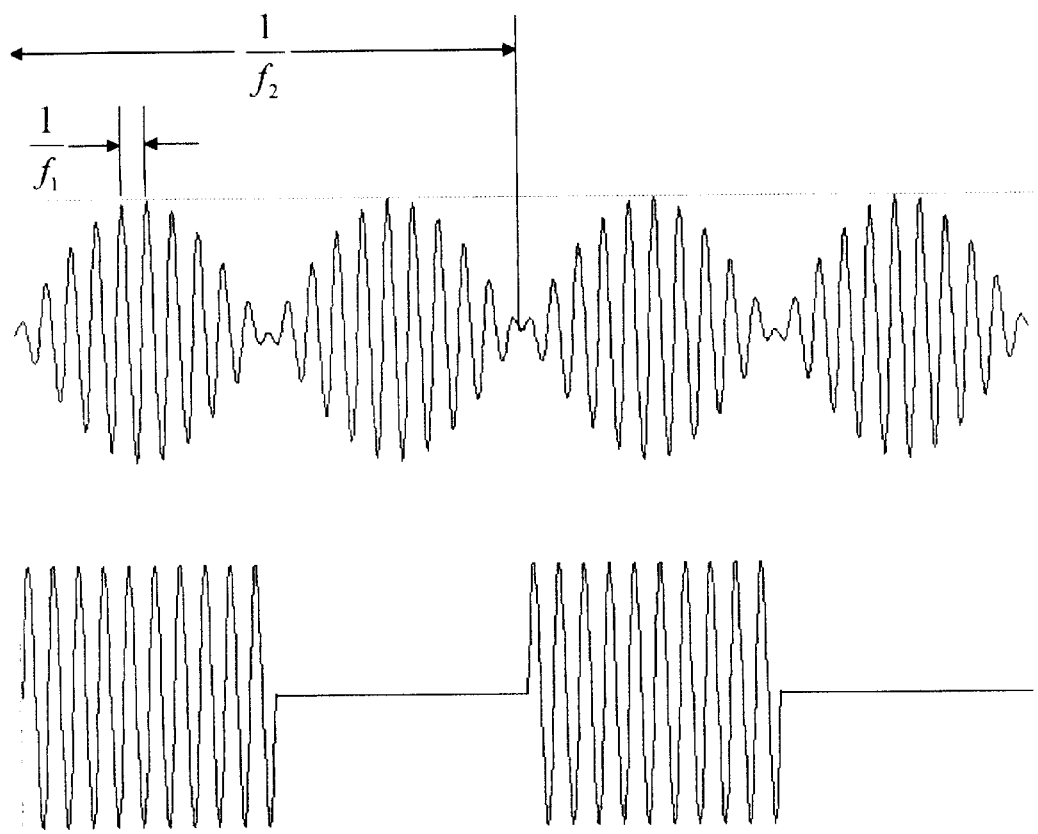
FIG. 3 shows how the excitation EM wave can be modulated to excite acoustic oscillations.

In one embodiment of the present invention the EM wave is modulated to improve coupling. FIG. 3 shows how the EM wave can be modulated to effectively excite acoustic oscillations using either sinusoidal or square wave modulation. The characteristic EM wave frequency $f_1$ is selected to effectively couple energy into the stent (typically 10 MHz to 10 GHz) whereas the low frequency modulation $f_2$ is selected to be near the stent acoustic resonance frequency (typically 100 kHz to 2 MHz). In an alternative embodiment, the EM wave is continuous at a single frequency $f_1$.

In one embodiment of the system, the control module 30 varies the transmitted EM wave frequency and modulation frequency over a selected range that covers all possible stent resonance frequencies. The acoustic receiver 60 detects the generated acoustic signal and the measured signal is digitized and recorded by the control module 30. The recorded data is processed by the control module 30 and displayed on a monitor 70. The control module can perform similar measurements for multiple EM wave polarizations and for different transmitter—acoustic receiver orientations.

In another embodiment of the system, the EM wave frequency and/or modulation frequency can be fixed and the generated acoustic spectrum measured over a range of acoustic frequencies (e.g., 100 kHz to 1 MHz). In another embodiment a short pulse (<1 nanosecond) EM pulse is used to gives the stent an impulse that generates broad-spectrum acoustic oscillations.

The data collected with the system for each patient immediately after stent implant is stored by the system in a data library for subsequent use. On a regular basis (e.g., every month) the patient returns to the doctor to have the complete set of measurements repeated. The new measurements are compared by the system to the original measurements collected after stent implant. If the change in signal indicates a significant change, the patient is scheduled for additional tests (e.g., angiography).

The approach of EM excitation and acoustic detection benefits from the fact that current ultrasound detectors have extreme sensitivity (*Ultrasound in Medicine*, Edited by F. A. Duck, A. C. Baker, H. C. Staritt, (1998)) and when coupled with acoustic lenses can localize the area being probed. In addition, since the frequency being excited is controlled by the EM modulation frequency, lock-in detection techniques may be used to enhance the signal to noise.

Figure 4:
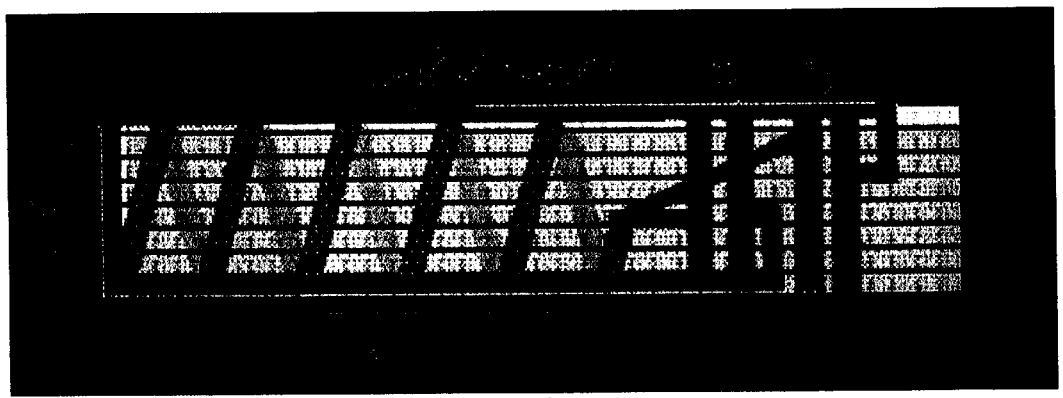
FIG. 4 shows a stent design that incorporates simple RF LRC resonant circuit plated onto a dielectric stent.

Although this technique is applicable to existing metallic stents, alternative stent designs can enhance the RF/acoustic signal and exhibit a narrow resonance frequency that can be more sensitive to restenosis formation. For example, FIG. 4 shows a different stent design where the stent has imprinted a resonance circuit tuned to a suitable RF frequency for easy coupling. In this case the resonant RF frequency of the stent will also change with restenosis formation due to the change in dielectric constant inside both the coil and near the fringe field of the patterned capacitors. For the stent in FIG. 4, the circuit resonance frequency is given by $$f = \frac{1}{2\pi}\sqrt{\frac{(C_1 + C_2)}{LC_1 C_2}}$$

where $C_1$, $C_2$ and L are the circuit capacitance and inductance respectively. Another approach to enhance the EM stent coupling is to manufacture the stent using Fractal antenna design that can widen the frequency sensitivity of the stent.

Circuit elements can also be employed to provide for harmonic generation of the RF excitation, such that a fundamental frequency may be employed to excite the imprinted circuit, where such fundamental is selected for advantageous absorption by the stent, or propagation to the stent, or interaction with the modes sensitive to restenosis, such that the imprinted circuit is capable of shifting the fundamental to another frequency, for example the second harmonic. The shifted frequency, for example a higher frequency, can thus provide for an enhanced interaction with features of the stent, or with those physical characteristic that are readily modified by restenosis. The shifted frequency is also more readily detected being easily filtered and detected with respect to the excitation.

Another embodiment of the invention uses the natural blood flow through the stent to excite the resonant acoustic modes stent. In such cases, the blood pressure and/or the magnetic flux through the stent excites the resonant acoustic modes of the stent, which would be detected without RF excitation. In addition, the RF excitation may be exchanged for acoustic excitation using pulsed or other noise reduction techniques to distinguish stent ringing over the excitation background.

Figure 5:
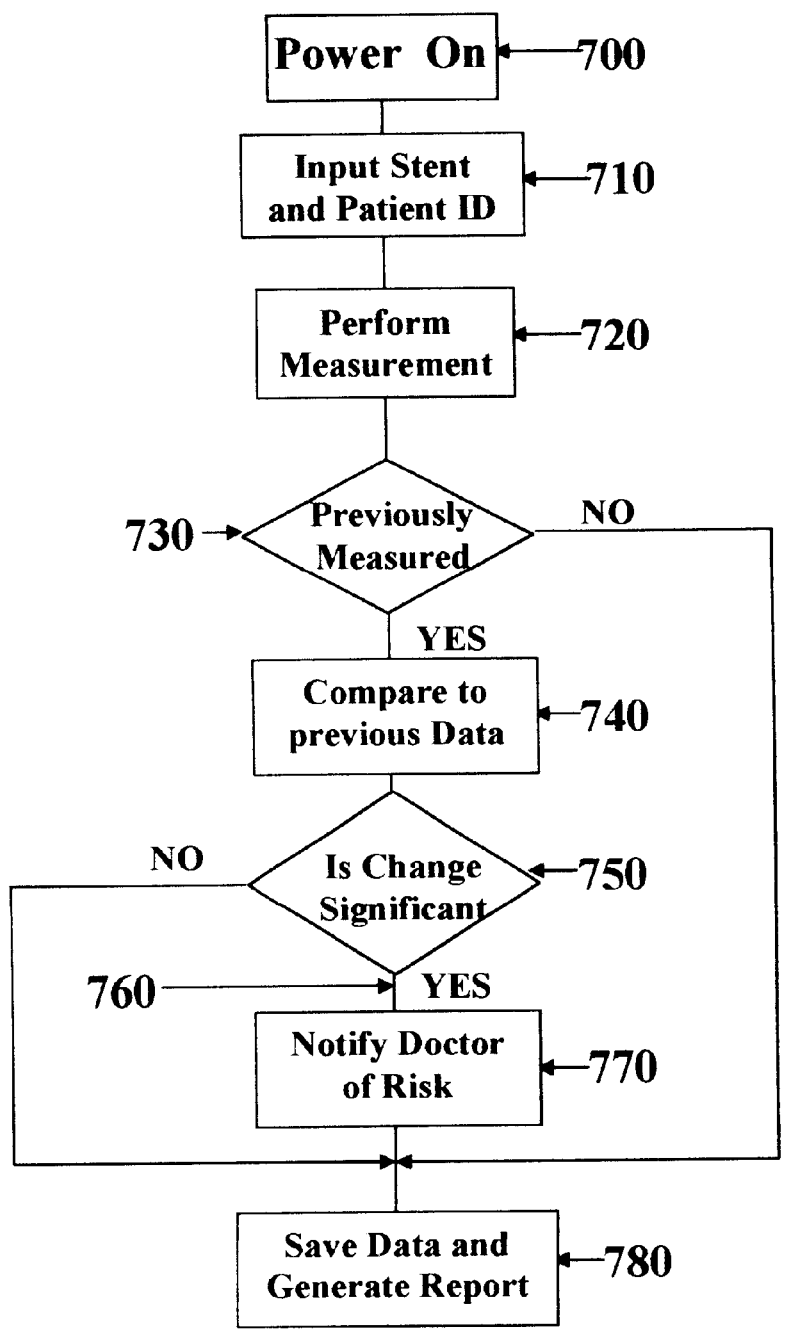
FIG. 5 shows a flow chart illustrating the key elements of an embodiment the system control software.

FIG. 5 shows a flow chart illustrating the key elements of an embodiment of the system control software. When first powered on (700) the system performs a self-test to verify that the system is operating correctly. If the system is operating correctly the computer asks the user for the stent type and patient ID (710) and whether a baseline reading for this patient already exists. The software then initiates a complete measurement (720) and records the data. The system then determines whether this is a first measurement or if previous data exists. If this is a baseline record (730), the software simply analyzes the data, verifies that signal levels and frequency range are suitable and records the data for future use. If previous records exist (740) for this patient the software then performs an analysis (750) of all the data to determine whether a dangerous change or trend exists that indicates possible restenosis 760. The results of the analysis are presented (e.g., to the doctor) (770) to enable interpretation of the data to provide a diagnosis. The data is saved and a report is generated 780.

The data collected by the system will be the acoustic signal as a function of carrier frequency and modulation frequency. In the analysis section the characteristic peaks in intensity are identified using standard peak detection algorithms well known in the art. The frequency of the peaks will be compared to the baseline measurement to calculate the frequency shifts. It is the magnitude of these frequency shifts that determine the extent of restenosis. A shift of 1–5% would indicate significant restenosis. If resonance peaks are broad, then a full spectral comparison between baseline and new data can be performed to calculate and difference index. Since the change in both electromagnetic and acoustic characteristics of the stent will be detected, the change in dielectric constant, acoustic impedance, and fill fraction of material growth inside the stent (restenosis) will be determined. Alternative analysis techniques could include neural networks that are trained with early clinical data.

In an alternative embodiment, a compact EM wave transmitter and acoustic receiver with reduced frequency range and options can be provided to the patient and used at home to monitor stent condition on a daily or weekly basis. This compact unit would be pre-tuned after the implantation for operation near the resonant frequency of the stent. As restenosis occurs, the detected signal amplitude decreases and if it decreases below an amplitude that has been pre-set, an alarm sounds. The alarm signal level is a function of stent type and the shape of the patient. In another embodiment, a selected individual or group such as a health care professional or organization could be automatically notified by wireless or hardwired technology that the preset amplitude had been reached or exceeded.

Although described for cardiovascular stents this technique can be applied to all applications where stents are used. This includes endovascular stents, neurovascular stents, and stents used for urological applications.

The above descriptions and illustrations are only by way of example and are not to be taken as limiting the invention in any manner. One skilled in the art can substitute known equivalents for the structures and means described. The full scope and definition of the invention, therefore, is set forth in the following claims.

We claim:

1. An apparatus, comprising:

a stent;

means for exciting said stent with an electromagnetic (EM) waves to produce an acoustic waves; and means for detecting said acoustic waves.

2. The apparatus of claim 1, further comprising means for analyzing said acoustic waves to determine if stent restenosis has occurred.

3. The apparatus of claim 1, wherein said means for exciting said stent comprises an EM wave transmitter capable of transmitting waves within a frequency range from 10 MHz to 10 GHz to excite acoustic oscillations in said stent.

4. The apparatus of claim 1, wherein said means for detecting said acoustic waves comprises an ultrasound detector.

5. The apparatus of claim 1, further comprising means for modulating said EM waves.

6. The apparatus of claim 2, wherein said means for analyzing said acoustic waves comprises a computer readable medium including software with an algorithm that determines if a change in acoustic spectrum has occurred and if so, uses said change to identify restenosis.

7. The apparatus of claim 3, further comprising EM wave transmitter includes a transmitter selected from the group consisting of a pair of coils, a single coil, a fractal antenna, an open dipole transmitter and a patch antenna.

8. The apparatus of claim 5, wherein said means for modulating said EM waves produces a modulation selected from the group consisting of a sinusoidal modulation and a square wave modulation.

9. The apparatus of claim 5, wherein said EM waves are modulated at a frequency selected to effectively couple energy into said stent.

10. The apparatus of claim 5, wherein said EM waves are modulated at a frequency selected to be near the stent acoustic resonance frequency.

11. The apparatus of claim 5, wherein said EM waves are modulated at a frequency within a range from about 100 kHz to about 2 MHz).

12. The apparatus of claim 4, further comprising an acoustic lens for directing acoustic waves onto said acoustic detector.

13. The apparatus of claim, wherein said means for detecting said acoustic waves includes a lock-in amplifier.

14. The apparatus of claim 1, wherein said stent comprises an electrically conductive portion.

15. The apparatus of claim 1, wherein said stent has an imprinted resonance circuit tuned to a RF frequency.

16. The apparatus of claim 1, wherein said algorithm comprises a peak detection algorithm.

17. A method for detecting in-stent restenosis, comprising:

exciting a stent with electromagnetic (EM) waves to produce an acoustic waves; and detecting said acoustic waves.

18. The method of claim 17, further comprising analyzing said acoustic waves to determine if stent restenosis has occurred.

19. The method of claim 17, wherein the step of exciting said stent comprises is carried out with EM waves within a frequency range from 10 MHz to 10 GHz.

20. The method of claim 17, further comprising modulating said EM waves.

21. The method of claim 18, wherein the step of analyzing said acoustic waves comprises determining if a change in acoustic spectrum has occurred to identify restenosis.

22. The method of claim 20, wherein the step of modulating said EM waves is carried out with a modulation selected from the group consisting of a sinusoidal modulation and a square wave modulation.

23. The method of claim 20, wherein said EM waves are modulated at a frequency selected to effectively couple energy into said stent.

24. The method of claim 20, wherein said EM waves are modulated at a frequency selected to be near the stent acoustic resonance frequency.

25. The method of claim 20, wherein said EM waves are modulated at a frequency within a range from about 100 kHz to about 2 MHz).

26. The method of claim 18, wherein the step of analyzing said acoustic waves is carried out with a peak detection algorithm.

* * * * *